United States Patent [19]

Sirrenberg et al.

[11] Patent Number: 4,711,905
[45] Date of Patent: Dec. 8, 1987

[54] 2,4-DIHALOGENOBENZOYL-(THIO)UREA INSECTICIDES

[75] Inventors: Wilhelm Sirrenberg, Sprockhoevel; Erich Klauke, Odenthal; Ingeborg Hammann, Mulheim; Wilhelm Stendel, Wuppertal, all of Fed. Rep. of Germany

[73] Assignee: Bayer Aktiengesellschaft, Leverkusen, Fed. Rep. of Germany

[21] Appl. No.: 746,554

[22] Filed: Jun. 19, 1985

Related U.S. Application Data

[62] Division of Ser. No. 489,901, Apr. 28, 1983, abandoned.

[30] Foreign Application Priority Data

May 11, 1982 [DE] Fed. Rep. of Germany ....... 3217619

[51] Int. Cl.$^4$ .................... A01N 47/34; C07C 127/22
[52] U.S. Cl. .................... 514/522; 514/517; 514/594; 558/50; 558/415; 560/18; 560/34; 564/44
[58] Field of Search .................... 564/44; 558/415, 50; 514/517, 522, 594; 560/18, 34

[56] References Cited

U.S. PATENT DOCUMENTS

| | | | |
|---|---|---|---|
| 3,992,553 | 11/1976 | Sirrenberg et al. | 424/304 |
| 4,005,223 | 1/1977 | Sirrenberg et al. | 424/322 |
| 4,068,002 | 1/1978 | Sirrenberg et al. | 424/322 |
| 4,139,636 | 2/1979 | Sirrenberg et al. | 424/322 |

FOREIGN PATENT DOCUMENTS 0042533 12/1981 European Pat. Off. ............ 549/366

*Primary Examiner*—Dolph H. Torrence
*Attorney, Agent, or Firm*—Sprung Horn Kramer & Woods

[57] ABSTRACT

A 2,4-dihalogenobenzoyl-(thio)urea of the formula

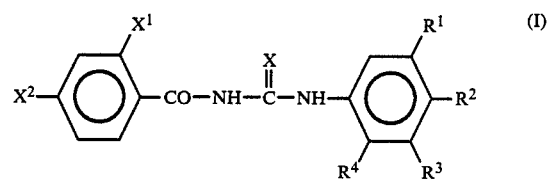

in which
X represents sulphur or oxygen,
$X^1$ and $X^2$ are identical or different and represent fluorine, chlorine, bromine or iodine,
$R^1$ represents hydrogen, halogen or optionally substituted radicals from the series comprising alkyl, alkoxy and alkylthio,
$R^2$ represents hydrogen, halogen, cyano, nitro, or optionally substituted radicals from the series comprising alkyl, alkylthio, alkylsulphonyl, alkoxy, aryloxy, alkylcarbonyl, alkoxycarbonyl, alkoxycarbonylalkyl and alkoxycarbonylalkylthio, or
$R^1$ and $R^2$ together represent an optionally substituted alkylenedioxy radical or —$CF_2$—O—$CF_2$—O—,
$R^3$ represents hydrogen, halogen or an optionally substituted alkyl, alkoxy or aryloxy radical, and
$R^4$ represents hydrogen, halogen, or optionally substituted radicals from the series comprising alkyl, alkylthio and alkoxy, with the exception of those cases in which X represents oxygen, $X^1$ and
$X^2$ represent chlorine and (a) $R^1$ represents chlorine, $R^2$ represents $OCF_2CHFCl$ and $R^3$ and $R^4$ represent hydrogen, or (b) $R^1$ represents chlorine, $R^2$ represents $OCF_3$ and $R^3$ and $R^4$ represent hydrogen, or (c) $R^1$ represents chlorine, $R^2$ represents $SCF_3$ and $R^3$ and $R^4$ represent hydrogen, or (d) $R^1$ represents $OCF_3$ and $R^2$, $R^3$ and $R^4$ represent hydrogen, or (e) $R^2$ represent $OCF_3$ and $R^1$, $R^3$ and $R^4$ represent hydrogen.

14 Claims, No Drawings

2,4-DIHALOGENOBENZOYL-(THIO)UREA INSECTICIDES

This is a division, of application Ser. No. 489,901, filed Apr. 28, 1983, now abandoned.

The present invention relates to new 2,4-dihalogenobenzoyl-(thio)ureas, ureas, several processes for their preparation and their use as pest-combating agents, in particular as insecticides.

It is already known that certain benzoylureas, such as, for example, 1-(2,6-difluorobenzoyl)-3-(4-chlorophenyl)-urea and 1-(2,6-difluorobenzoyl)-3-(4-trifluoromethylphenyl)-urea, possess insecticidal properties (see, for example, DE-AS (German Published Application) No. 2,123,236 and the corresponding U.S. Pat. No. 3,933,908 and U.S. Pat. No. 4,139,636, and the 2- and 2,6-substituted benzoylureas and -thioureas have been described as being particularly insecticidally active.

The new 2,4-diahalogenobenzoyl-(thio)ureas of the formula I

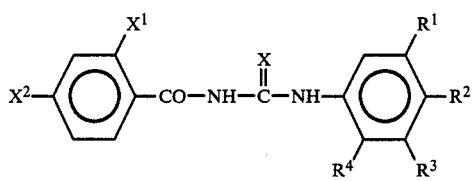

in which
X represents sulphur or oxygen,
$X^1$ and $X^2$ are identical or different and represent fluorine, chlorine, bromine or iodine,
$R^1$ represents hydrogen, halogen or optionally substituted radicals from the series comprising alkyl, alkoxy and alkylthio,
$R^2$ represents hydrogen, halogen, cyano, nitro, or optionally substituted radicals from the series comprising alkyl, alkylthio, alkylsulphonyl, alkoxy, aryloxy, alkylcarbonyl, alkoxycarbonyl, alkoxycarbonylalkyl or alkoxycarbonylalkylthio, or
$R^1$ and $R^2$ together represent an optionally substituted alkylenedioxy radical or —$CF_2$—O—$CF_2$—O—,
$R^3$ represents hydrogen, halogen or an optionally substituted alkyl, alkoxy or aryloxy radical, and $R^4$ represents hydrogen, halogen, or optionally substituted radicals from the series comprising alkyl, alkylthio or alkoxy, with the exception of those cases in which X represents oxygen, $X^1$ and $X^2$ represent chlorine and (a) $R^1$ represents chlorine, $R^2$ represents $OCF_2CHFCL$ and $R^3$ and $R^4$ represent hydrogen, or (b) $R^1$ represents chlorine, $R^2$ represents $OCF_3$ and $R^3$ and $R^4$ represent hydrogen, or (c) $R^1$ represents chlorine, $R^2$ represents $SCF_3$ and $R^3$ and $R^4$ represent hydrogen, or (d) $R^1$ represents $OCF_3$ and $R^2$, $R^3$ and $R^4$ represent hydrogen, or (e) $R^2$ represents $OCF_3$ and $R^1$, $R^3$ and $R^4$ represent hydrogen,
have been found.

These new compounds have powerful biological, in particular insecticidal, properties, which make it possible to use them as pest-combating agents, in particular as insecticides.

Furthermore, it has been found that the new 2,4-dihalogenobenzoylureas of the formula (I) are obtained by a process in which (a) substituted anilines of the formula II

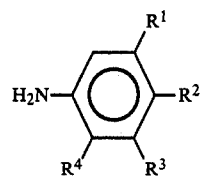

in which
$R^1$, $R^2$, $R^3$ and $R^4$ have the meanings given above, are reacted with benzoyl iso(thio)cyanates of the formula III

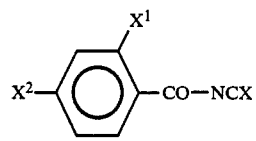

in which
X, $X^1$ and $X^2$ have the meanings given above,
if appropriate in the presence of a diluent, or
(b) substituted phenyl iso(thio)cyanates of the formula IV

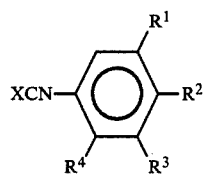

in which
$R^1$, $R^2$, $R^3$, $R^4$ and X have the meanings given above, are reacted with benzoic acid amides of the formula V

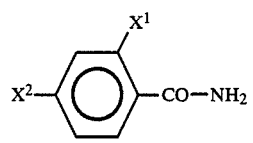

in which
$X^1$ and $X^2$ have the meanings given above,
if appropriate in the presence of a catalyst and, if appropriate, in the presence of a diluent.

Optionally substituted alkyl $R^1$, $R^2$, $R^3$ and $R^4$ represent straight-chain or branched alkyl having 1 to 12, preferably 1 to 6, in particular 1 to 4, carbon atoms. Optionally substituted methyl, ethyl, n- and i-propyl and n-, i-, sec.- and tert.-butyl may be mentioned as examples.

Optionally substituted alkoxy $R^1$, $R^2$, $R^3$ and $R^4$ represent straight-chain or branched alkoxy having preferably 1 to 6, in particular 1 to 4, carbon atoms. Optionally substituted methoxy, ethoxy, n- and i-propoxy and n-, i-, sec.- and tert.-butoxy may be mentioned as examples.

Optionally substituted alkylthio $R^1$, $R^2$ and $R^4$ and alkylsulphonyl $R^2$ represent straight-chain or branched alkylthio or alkylsulphonyl having pererably 1 to 6, in particular 1 to 4, carbon atoms. Optionally substituted methylthio, ethylthio, n- and i-propylthio, n-, i-, sec.- and tert.-butylthio, methylsulphonyl, ethylsulphonyl, n- and i-propylsulphonyl and n-, i-, sec.- and tert.-butylsulphonyl may be mentioned as examples.

Optionally substituted aryloxy $R^2$ and $R^3$ preferably contains 6 or 10 carbon atoms in the aryl part, and phenoxy and naphthyloxy, preferably phenoxy, may be mentioned.

Optionally substituted alkylcarbonyl, alkoxycarbonyl, alkoxycarbonylalkyl or alkoxycarbonylalkylthio $R^2$ corresponds in its alkyl part of the alkyl radical $R^2$, in its alkoxy part to the alkoxy radical $R^2$ and in its alkylthio part to the alkylthio radical $R^2$.

Optionally substituted alkylenedioxy in the definition of $R^1$ and $R^2$ contains preferably 1 to 3, in particular 1 or 2, carbon atoms.

Halogen denotes (where not stated otherwise) fluorine, chlorine, bromine and iodine, preferably fluorine, chlorine and bromine.

The radicals $R^1$, $R^2$, $R^3$ and $R^4$ can be monosubstituted or polysubstituted by identical or different substituents. Preferred substituents in this case are: halogen, the halogen atoms being identical or different and preferably being fluorine, chlorine or bromine, in particular fluorine or chlorine; cyano, nitro, phenyl, alkyl having preferably 1 to 4 carbon atoms, alkylthio, alkylthioalkyl and/or alkylsulphonyloxy having preferably 1 to 4 carbon atoms, halogenoalkyl, halogenoalkoxy and/or halogenoalkylthio having preferably 1 to 2 cabon atoms and preferably 1 to 5, in particular 1 to 3, halogen atoms, the halogen atoms being identical or different and being preferably fluorine, chlorine or bromine, in particular fluorine, such as trifluoromethyl, trifluoromethoxy or trifluoromethylthio; and alkoxycarbonyl having 1 to 6 carbon atoms in the alkyl part.

X preferably represents oxygen.

$X^1$ preferably represents chlorine and $X^2$ preferably represents fluorine.

The new compounds of the formula (I) have properties which make it possible to use them as pest-combating agents; in particular, they are distinguished by an outstanding insecticidal activity.

The invention preferably relates to new compounds of the formula (I) in which

X represents sulphur or oxygen, $X^1$ and $X^2$ are indentical or different and represent fluorine, chlorine or bromine, $X^1$ preferably representing chlorine and $X^2$ preferably representing fluorine, $R^1$ represents hydrogen, halogen, or an optionally halogen-substituted radical from the series comprising $C_1$–$C_6$-alkyl, $C_1$–$C_6$-alkoxy and $C_1$–$C_6$-alkylthio, $R^2$ represents hydrogen, cyano, nitro, halogen, or an optionally halogen-substituted radical from the series comprising $C_1$–$C_6$-alkyl, $C_1$–$C_6$-alkylthio, $C_1$–$C_6$-alkylsulphonyl, $C_1$–$C_6$-alkoxy, $C_1$–$C_6$-alkylcarbonyl, $C_1$–$C_6$-alkoxycarbonyl, $C_1$–$C_6$-alkoxycarbonylalkyl and $C_1$–$C_6$-alkoxycarbonylalkylthio, or a phenoxy which is optionally substituted by halogen, cyano, nitro, trifluoromethyl, tri-fluoromethoxy, trifluoromethylthio, $C_1$–$C_4$-alkyl, $C_1$–$C_4$-alkylthio, $C_1$–$C_4$-alkylthioalkyl, $C_1$–$C_4$-alkylsulphonyloxy, phenyl and/or $C_1$–$C_4$-alkoxycarbonyl, or $R^1$ and $R^2$ together represent alkylene-dioxy which has 1 to 3 carbon atoms and is optionally substituted by fluorine and/or chlorine, or represent —$CF_2$—O—$CF_2$—O, $R^3$ represents hydrogen, halogen, or an optionally halogen-substituted $C_1$–$C_6$-alkyl, $C_1$–$C_6$-alkoxy or phenoxy radical, and $R^4$ represents hydrogen, halogen, or optionally halogen-substituted radicals from the series comprising $C_1$–$C_6$-alkyl, $C_1$–$C_6$-alkylthio or $C_1$–$C_6$-alkoxy, with the exception of those cases in which X represents oxygen, $X^1$ and $X^2$ represent chlorine and (a) $R^1$ represents chlorine, $R^2$ represents $OCF_2CHFCL$ and $R^3$ and $R^4$ represent hydrogen, or (b) $R^1$ represents chlorine, $R^2$ represents $OCF_3$ and $R^3$ and $R^4$ represent hydrogen, or (c) $R^1$ represents chlorine, $R^2$ represents $SCF_3$ and $R^3$ and $R^4$ represent hydrogen, or (d) $R^1$ represents $OCF_3$ and $R^2$, $R^3$ and $R^4$ represent hydrogen, or (e) $R^2$ represents $OCF_3$ and $R^1$, $R^3$ and $R^4$ represent hydrogen, halogen in each case representing fluorine, chlorine, bromine and/or iodine, preferably fluorine, chlorine and/or bromine.

Particularly preferred compounds of the formula (I) are those in which

X represents oxygen or sulphur, $X^1$ and $X^2$ are identical or different and represent fluorine, chlorine or bromine, $X^1$ preferably representing chlorine and $X^2$ preferably representing fluorine, $R^1$ represents hydrogen, fluorine, chlorine, bromine, methyl, trifluoromethyl, difluoromethyl, 2-chloro-1,1,2-trifluoroethoxy or trifluoromethylthio, $R^2$ represents hydrogen, chlorine, bromine, fluorine, cyano, nitro, methyl, ethyl, n-propyl, i-propyl, n-butyl, i-butyl, sec.-butyl, tert.-butyl, trifluoromethyl, difluoromethyl, 1,1-difluoroethyl, 1,1,2,2,2-pentafluoroethyl, trifluoromethoxy, difluoromethoxy, chlorodifluoromethoxy, 2-chloro-1,1,2-trifluoroethoxy, 1,1,2,2-tetra-fluoroethoxy, 2,2-dichloro-1,1-difluoroethoxy, 1,1,2,3,3,3-hexafluoropropoxy, trifluoromethylthio, difluoromethylthio, chlorodifluoromethylthio, 2-chloro-1,1,2-trifluoroethylthio, methoxycarbonyl-difluoromethylthio, 1,1,2,3,3-hexafluoropropylthio, trifluoromethylsulphonyl, and methoxy-, ethoxy-, n-propoxy-, i-propoxy-, n-butoxy-, i-butoxy-, sec.-butoxy and tert.-butoxycarbonyl, or phenoxy which is optionally substituted by halogen, nitro, cyano, $C_1$–$C_4$-alkyl, $C_1$–$C_4$-alkylthio, $C_1$–$C_4$-alkyl-thioalkyl, $C_1$–$C_4$-alkylsulphonyloxy, $C_1$–$C_6$-halogenoalkyl, phenyl and/or $C_1$–$C_6$-alkoxycarbonyl, or $R^1$ and $R^2$ together represent difluoromethylenedioxy or represent ethylenedioxy which is substituted by 3 or 4 fluorine atoms or by 3 fluorine atoms and 1 chlorine atom, or represent —$CF_2$—O—$CF_2$—O—, $R^3$ represents hydrogen, fluorine, chlorine, bromine, methyl or trifluoromethyl, and $R^4$ represents hydrogen, chlorine, bromine, trifluoromethyl, trifluoromethoxy and trifluoromethyl-thio, with the exception of those cases in which X represents oxygen, $X^1$ and $X^2$ represent chlorine and (a) $R^1$ represents chlorine, $R^2$ represents $OCF_2CHCFCL$ and $R^3$ and $R^4$ represent hydrogen, or (b) $R^1$ represents chlorine, $R^2$ represents $OCF_3$ and $R^3$ and $R^4$ represent hydrogen, or (c) $R_1$ represents chlorine, $R^2$ represents $SCF_3$ and $R^3$ and $R^4$ represent hydrogen, or (d) $R^2$ represents $OCF_3$ and $R^1$, $R^3$ and $R^4$ represent hydrogen.

Very particularly preferred compounds of the formula (I) are those in which

X represents oxygen, $X^1$ represents chlorine, $X^2$ represents fluorine, $R^1$ represents hydrogen or chlorine, $R^2$ represents hydrogen, trifluoromethyl, trifluoromethoxy, chlorodifluoromethoxy, chlorotrifluoroethoxy, n-pentafluoropropoxy, trifluoromethylthio, chlorodifluoromethylthio, 4-nitrophenoxy, 4-cyanophenoxy and 4-trifluoromethylphenoxy, or $R^1$ and $R^2$ together represent chlorotrifluoro-ethylenedioxy or —$CF_2$—O—$CF_2$—O—, $R^3$ represents hydrogen or chlorine, and $R^4$ represents hydrogen.

If 3-chloro-4-trifluoromethoxyaniline and 2-chloro-4-fluoro-benzoyl isocyanate are used as starting materials, according to process variant (a), the course of the reaction can be represented by the following equation:

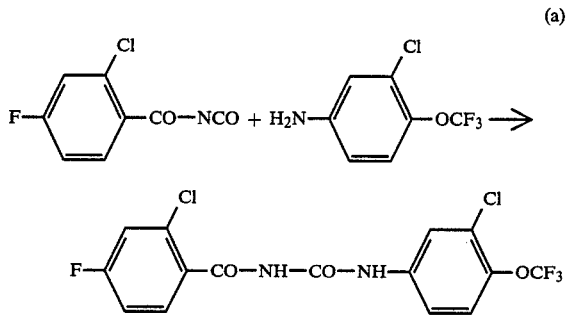

(a)

If 3-chloro-4-trifluoromethoxyphenyl isocyanate and 2-chloro-4-fluorobenzamide are used as starting materials, according to process variant (b), the course of the reaction can be represented by the following equation:

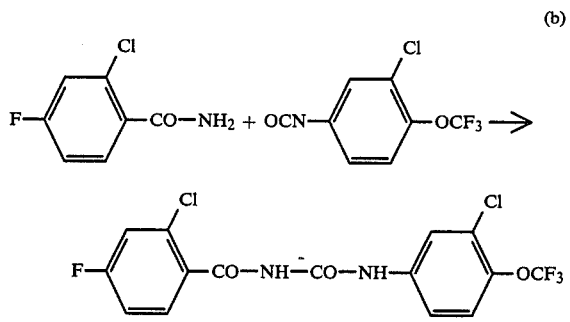

(b)

The following may be mentioned as examples of the compounds of the formula (II): 4-trifluoromethoxy-, 3,4-chlorotrifluoroethylenedioxy-, 4-trifluoromethylthio-, 3-chloro-4-chlorodifluoromethylthio-, 3-chloro-4-chlorotrifluoroethoxy-, 4-chloro-, 4-trifluoromethyl-, 3,4-dichloro-, 4-pentafluoropropoxy-, 4-methyl-, 4-ethyl-, 4-n-propyl-, 4-i-propyl-, 4-n-butyl-, 4-i-butyl-, 4-sec.-butyl-, 4-tert.-butyl-, 3,5-dichloro-, 4-chlorodifluoromethoxy-, 3-chloro-4-trifluoromethoxy-, 4-chlorotrifluoroethoxy-, 3-chloro-4-trifluoromethylthio-, 4-bromo-, 2-bromo-, 3-chloro-4-nitrophenoxy-, 3,5-dichloro-4-(4-nitrophenoxy, 3,4,6-trichloro-, 2-chloro-, 3-chloro-4-trifluoromethyl-, 2-trifluoromethoxy-, 3,5-dichloro-4-(4-cyanophenoxy)-, 3,5-dichloro-4-(4-trifluoromethylphenoxy)-, 3,5-dichloro-4-(2-chloro-4-trifluoromethylphenoxy)- and 4-fluoro-aniline.

The substituted anilines of the formula (II) which are to be used as starting materials are known and can be prepared by processes and methods which are known from the Literature (see U.S. Pat. Nos. 4,139,636; 4,277,499; 4,234,600; 4,348,323; 4,234,600; U.S. Ser. No. 268,961, filed June 1, 1981, now pending).

The following may be mentioned as examples of the compounds of the formula (III): 2-chloro-4-fluoro-benzoyl isocyanate and -benzoyl isothiocyanate, and 2-bromo-4-fluoro-benzoyl isocyanate and -benzoyl isothiocyanate.

The starting compounds of the formula (III) are known.

The following may be mentioned as examples of the compounds of the formula (IV): 4-trifluoromethoxy-, 4-trifluoromethyl-, 4-trifluoromethylthio-, 3-chloro-4-trifluoromethoxy-, 3-chloro-4-trifluoromethyl-, 3-chloro-4-trifluoromethylthio-, 3, 4-chlorotrifluoroethylenedioxy-, 3-chloro-4-chlorodifluoromethylthio-, 3-chloro-4-chlorotrifluoroethoxy-, 4-chloro-, 2-chloro-, 3,4-dichloro-, 4-pentafluoropropoxy-, 4-methyl-, 4-ethyl-, 4-n-propyl-, 4-i-propyl-, 4-n-butyl-, 4-i-butyl-, 4-sec.-butyl-, 4-tert.-butyl-, 3,5-dichloro-, 4-chlorotrifluoromethoxy-, 3-chloro-4-trifluoromethoxy-, 4-chlorotrifluoroethoxy-, 3-chloro-4-trifluoromethylthio-, 2-bromo-, 4-bromo-, 3-chloro-4-nitrophenoxy-, 3,5-dichloro-4-(4-nitrophenoxy)-, 3,4,6-trichloro-, 2-trifluoromethoxy-, 3,5-dichloro-4-(4-cyano-phenoxy)-, 3,5-dichloro-4-(4-trifluoromethylphenoxy)-, 3,5-dichloro-4-(2-chloro-4-trifluoromethylphenoxy)- and 4-fluoro-phenyl iso(thio)cyanate.

Compounds of the formula (IV) are known and can be prepared by generally known processes and methods.

The following may be mentioned as examples of the compounds of the formula (V): 2-chloro-4-fluoro-benzoic acid amide and 2-bromo-4-fluoro-benzoic acid amide.

Compounds of the formula (V) are known and can be obtained by generally known methods and processes (see z. obsc-chim. 11 (1941), 243; and C.A. 1941, 7965).

Suitable diluents are virtually all inert organic solvents. These include in particular aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylacetamide and N-methyl-pyrrolidone, and tetramethylenesulphone.

Tertiary amines, such as triethylamine and 1,4-diazabicyclo[2,2,2]-octane, and organic tin compounds, such as, for example, dibutyl-tin dilaurate, can preferably be used as catalysts for the reaction according to process variant (b).

The reaction temperature can be varied within a relatively wide range. In general, process variant (a) is carried out at between 20° and 180° C., preferably between 60° and 120° C., and process variant (b) at between 20° and 200° C., preferably between 60° and 190° C. The process variants according to the invention are carried out in general at atmospheric pressure.

To carry out the process variant according to the invention, the starting materials are usually employed in about equimolar amounts. An excess of one or the other of the reaction components has no substantial advantages.

The reaction products are worked up by customary methods, for example by filtering off the precipitated product under suction, or by dissolving out undesired by-products from the reaction mixture. They are characterized by their melting point.

The active compounds are very suitable for combating animal pests, especially insects, very particularly preferably for combating insects which are encountered in agriculture, in forestry, in the protection of stored products and of materials, and in the hygiene field. They are active against normally sensitive and resistant species and against all or some stages of development. The above-mentioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, Lepisma saccharina. From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata. Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithoeolletis blancardella, Hypnomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp. *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudo spretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis and Costelytra zealandica.* From the order of the Hymenoptera, for example, Diprion spp., Hoplocampa spp., Lasius spp., *Monomorium pharaonis* and Vespa spp. From the order of the Diptera, for example, Aëdes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The new active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: strongly polar solvents, such as dimethylformamide and dimethylsulphoxide; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attopulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as disperising agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphate, phenylureas, substances produced by microorganisms and others.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 90% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates (substrates coated with lime).

The active compounds according to the invention are also suitable for combating ectoparasites and endoparasites in the field of livestock husbandry and livestock breeding, and it is possible to achieve better results, for example higher milk outputs, higher weight, more attractive animal skin, longer life span, etc., by combating the pests.

The active compounds according to the invention are used in a known manner in these fields, such as by external application, for example in the form of dipping, spraying, pouring on and spotting on, and dusting, and by oral administration, for example via the feed or drinking water, for example in the form of tablets, capsules, drinks and granules.

The activity of the substances according to the invention is illustrated by the examples which follow.

The compounds which correspond to formula (I) and have aniline radicals such as those contained in the compounds described in DE-AS (German Published Specifications) Nos. 2,123,236 and 3,041,947; European Patent Specifications Nos. 6,184, 7,687, 8,768, 13,414, 14,674, 14,675, 14,676, 16,729, 23,884, 25,363, 30,158, 31,974, 33,231, 35,084, 38,776, 40,179, 44,278 and 44,410 and Japanese Patent Specifications Nos. 55,011,537, 56,015,272 and 56,092,857 also possess, as 2,4-dihalogeno-benzoyl(thio)urea derivatives, an insecticidal activity.

EXAMPLE A

Plutella test

Solvent: 3 parts by weight of dimethylformamide.
Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water to the desired concentration.

Cabbage Leaves (*Brassica oleracea*) are treated by being dipped into the preparation of active compound of the desired concentration and are infested with caterpillars of the diamond-back moth (*Plutella maculipennis*), as long as the leaves are still moist.

After the specified periods of time, the destruction in % is determined. 100% means that all the caterpillars have been killed; 0% means that none of the caterpillars have been killed (control).

In this test, for example, the compounds of Preparation Examples (3), (4), (9), (11), (12), (13), (14), (34), (15), (17), (19), (22), (30), (35), (37), (39), (42), (43), (40), (47), (49), (54), (57), (59), (61) a. (66) show a degree of destruction of 100% after 7 days, for example at an active compound concentration of 0.001%.

EXAMPLE B

Test with parasite fly larvae (Lucilia cuprina)

Solvent: 35 parts by weight of ethylene glycol monomethyl ether.
Emulsifier: 35 parts by weight of nonylphenol; polyglycol ether.

To produce a suitable preparation of active compound, 30 parts by weight of the particular active substance are mixed with the stated amount of solvent which contains the abovementioned amount of emulsifier, and the concentrate thus obtained is diluted with water to the desired concentration.

About 20 fly larvae (*Lucilia cuprina*) are introduced into a test tube which contains approx. 2 cm$^3$ of horse muscle. 0.5 ml of the preparation of active compound are introduced onto this horse muscle. After 24 hours, the degree of destruction in % is determined. 100% means that all the larvae have been killed, and 0% (control) means that none of the larvae have been killed.

In a test, for example, with an active compound concentration of 100 ppm, for example the compounds of Preparation Examples (4), (5), (8), (12) and (19) showed a destruction of 100%.

The preparation examples which follow are intended to illustrate the preparation of the new compounds:

EXAMPLE 1

(Process variant a)

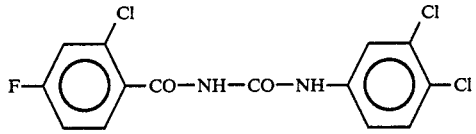

3.24 g (0.02 mol) of 3,4-dichloroaniline are dissolved in 60 ml of dry toluene, and 3.99 g (0.02 mol) of 2-chloro-4-fluoro-benzoyl isocyanate are added in the absence of moisture. The mixture is stirred for one hour at 80° C. and then cooled to 20°-25° C. The precipitate which separates out is filtered off under suction and dried in vacuo at 100° C. 6.8 g (94% of theory) of 1-(2-chloro-4-fluoro-benzoyl)-3-(3,4-dichlorophenyl)-urea of melting point 208° C. are obtained.

EXAMPLE 2

(Process variant b)

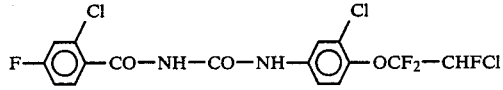

3.47 g (0.02 mol) of 2-chloro-4-fluorobenzamide and 7.2 g (0.022 mol) of 3-chloro-4-(2-chloro-1,1,2-trifluoro-ethoxy)-phenyl isocyanate are melted for two hours at 180° C., in the presence of one drop of dibutyl-tin dilaurate. After the mixture has been cooled, the solid product is comminuted in hot methanol, and the product is filtered off under suction and dried. 7.2 g (76.5% of theory) of 1-(2-chloro-4-fluoro-benzoyl)-3-(3-chloro-4-(2-chloro-1,1,2-trifluoro-ethoxy)-phenyl)-urea of melting point 186° C. are obtained.

The compounds of the formula (Ia) which are listed in the table below can be prepared analogously to Example 1 and 2.

TABLE

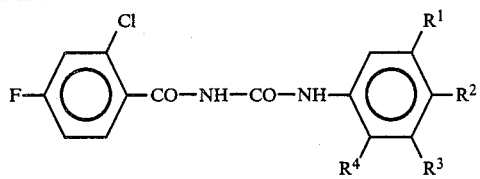

| Example No. | $R^1$ | $R^2$ | $R^3$ | $R^4$ | Melting point (°C.) |
|---|---|---|---|---|---|
| 3 | H | SCF$_3$ | H | H | 155 |
| 4 | Cl | SCF$_2$Cl | H | H | 149 |
| 5 | —O—CF$_2$—CFCl—O— | | H | H | 158 |
| 6 | H | Cl | H | H | 205 |
| 7 | H | CF$_3$ | H | H | 180 |
| 8 | H | OCF$_3$ | H | H | 170 |
| 9 | H | —O—CF$_2$—CHF—CF$_3$ | H | H | 147 |
| 10 | H | —C(CH$_3$)$_3$ | H | H | 209 |
| 11 | Cl | H | Cl | H | 233 |
| 12 | H | OCF$_2$Cl | H | H | 157 |
| 13 | Cl | OCF$_3$ | H | H | 179 |
| 14 | H | OCF$_2$CHClF | H | H | 165 |
| 15 | Cl | SCF$_3$ | H | H | 164 |
| 16 | H | Br | H | H | 213 |
| 17 | Cl | —O—⌬—NO$_2$ | Cl | H | 214 |
| 18 | Cl | Cl | H | Cl | 214 |
| 19 | Cl | CF$_3$ | H | H | 204 |
| 20 | H | H | H | OCF$_3$ | 127 |
| 21 | CF$_3$ | H | CF$_3$ | H | 169 |
| 22 | CF$_3$ | Cl | H | H | 158 |
| 23 | H | —OCF$_2$—CHCl$_2$ | H | H | 126 |
| 24 | CF$_3$ | SCH$_3$ | H | H | 166 |
| 25 | CF$_3$ | OCH$_3$ | H | H | 194 |
| 26 | CF$_3$ | CH$_3$ | H | H | 170 |
| 27 | CF$_3$ | H | H | CF$_3$ | 154 |
| 28 | H | F | H | H | 211 |
| 29 | —O—CF$_2$—CHFCl | Cl | H | H | 138 |
| 30 | Cl | —O—⌬—CN | Cl | H | 230 |
| 31 | H | NO$_2$ | H | H | 223 |
| 32 | H | OCHF$_2$ | H | H | 169 |

TABLE-continued
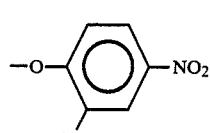
(Ia)
| Example No. | R¹ | R² | R³ | R⁴ | Melting point (°C.) |
|---|---|---|---|---|---|
| 33 | $CF_3$ | H | H | H | 167 |
| 34 | Cl | 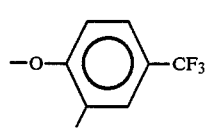 | Cl | H | 233 |
| 35 | $CF_3$ | F | H | H | 167 |
| 36 | H | 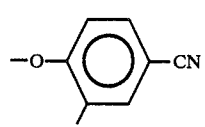 | H | H | 186 |
| 37 | $CHF_2$ | Cl | H | H | 149 |
| 38 | H | $-COOC(CH_3)_3$ | H | H | 187 |
| 39 | H | $-SO_2CF_3$ | H | H | 178 |
| 40 | Cl | 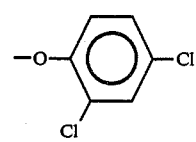 | H | H | 203 |
| 41 | H | $CF_3$ | H | Cl | 181 |
| 42 | H | 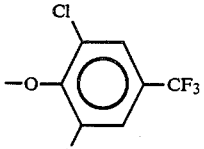 | Cl | H | 192 |
| 43 | H | $-S-CF_2-CCl_2-CH_3$ | H | H | 177 |
| 44 | H | 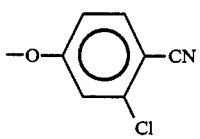 | H | H | 210 |
| 45 | $-OCF_2-CHFCl$ | H | H | H | 99 |
| 46 | $SCF_3$ | H | H | H | 104 |
| 47 | Cl | 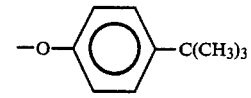 | Cl | H | 228 |
| 48 | Cl |  | Cl | H | 209 |

TABLE-continued $$\text{(Ia)}\quad \underset{F}{\overset{Cl}{\bigcirc}}-CO-NH-CO-NH-\underset{R^4\ R^3}{\overset{R^1\ R^2}{\bigcirc}}$$

| Example No. | R¹ | R² | R³ | R⁴ | Melting point (°C.) |
|---|---|---|---|---|---|
| 49 | Br | —O—C₆H₃(Cl) (4-Cl-phenoxy) | CH₃ | H | 198 |
| 50 |  | —O—CF₂—CHF—O— | H | Cl | 202 |
| 51 | Cl | —O—C₆H₄—C₆H₅ (4-phenyl-phenoxy) | Cl | H | 208 |
| 52 | H | —O—C₆H₃(Cl)(CN) (3-Cl-4-CN-phenoxy) | H | H | 202 |
| 53 | H | —O—C₆H₄—CF₃ (4-CF₃-phenoxy) | H | H | 184 |
| 54 |  | —O—CF₂—O— | H | H | 172 |
| 55 |  | —O—CF₂—O— | H | Cl | 214 |
| 56 |  | —O—CF₂—O— | H | CF₃ | 172 |
| 57 |  | —O—CF₂—CHF—O— | H | H | 178 |
| 58 | Cl | —O—C₆H₄—OSO₂—CH₃ | Cl | H | 196 |
| 59 | CH₃ | —O—C₆H₄—Cl (4-Cl-phenoxy) | CH₃ | H | 202 |
| 60 | Cl | —O—C₆H₄—CH₂—S—C₂H₅ | Cl | H | 162 |
| 61 | Cl | —O—C₆H₄—OCF₃ | Cl | H | 185 |
| 62 | Cl | —O—C₆H₄—SCF₃ | Cl | H | 163 |
| 63 | Cl | —CO—O—CH₂CF₃ | H | H | 158 |

TABLE-continued

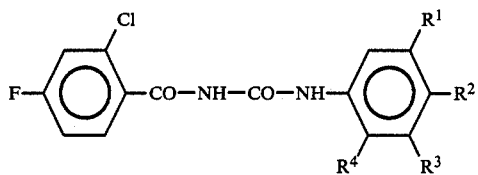

| Example No. | R¹ | R² | R³ | R⁴ | Melting point (°C.) |
|---|---|---|---|---|---|
| 64 | Cl | -O-⟨C₆H₂(CH₃)₂(SCH₃)⟩ | Cl | H | 218 |
| 65 | Cl | -O-⟨C₆H₃(Cl)(OCF₃)⟩ | Cl | H | 186 |
| 66 | —CF₂—O—CF₂—O— | | H | H | 144 |

The preparation of the starting materials of the formula V may be described with reference to 2-chloro-4-fluoroenzamide:

(a) 573 g of 2-chloro-4-fluorotoluene are chlorinated at 100°–140° C. under UV irradiation, until a refractive index of $n_D^{20}$ 1.5590 is reached. Working up by distillation gives:

978 g of 2-chloro-4-fluoro-benzotrichloride of b.p.: 120° C./20 mbar $n_D^{20}$: 1.5625.

(b) 124 g of the chloro-fluorobenzotrichloride are initially introduced and heated to 120° C., and 0.1% of FeCl₃ is added, followed by the dropwise addition of 9 g of H₂O. Vigorous evolution of HCl begins, and this is complete after ½ hour. Working up by distillation.

Yield 65 g.

b.p. 96° C./15 mbar $n_D^{20}$: 1.5522.

(c) The acid-chloride is added dropwise, at 30° C., to an excess of approx. 12% strength NH₃/water solution, and the mixture is stirred vigorously. The precipitated crystals are filtered off.

60 g of 2-chloro-4-fluoro-benzamide of m.p.: 149°–51° are obtained from 70 g of acid-chloride.

The remaining starting materials of the formula V can be obtained by the same method.

It will be understood that the specification and examples are illustrative but not limitative of the present invention and that other embodiments within the spirit and scope of the invention will suggest themselves to those skilled in the art.

We claim:

1. A 2,4-dihalogenobenzoyl-(thio)urea of the formula

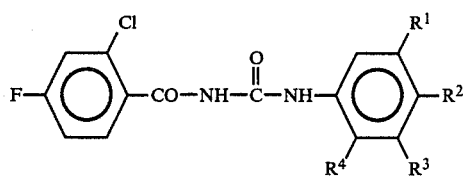

in which
R¹ represents hydrogen, halogen, or an optionally halogen-substituted radical from the series comprising C₁–C₆-alkyl, C₁–C₆-alkoxy and C₁–C₆-alkylthio, R² represents a phenoxy which is optionally substituted by halogen, cyano, nitro, trifluoromethyl, trifluoromethoxy, trifluoromethylthio, C₁–C₄-alkyl, C₁–C₄-alkylthio, C₁–C₄-alkylthioalkyl, C₁–C₄-alkylsulphonyloxy, phenyl and/or C₁–C₄-alkoxycarbonyl, R³ represents hydrogen, halogen, or an optionally halogen-substituted C₁–C₆-alkyl, C₁–C₆-alkoxy or phenoxy radical, and R⁴ represents hydrogen, halogen, or optionally halogen-substituted radicals from the series comprising C₁–C₆-alkyl, C₁–C₆-alkylthio and C₁–C₆-alkoxy.

2. A compound according to claim 1, in which
R¹ represents hydrogen or chlorine,
R² represents phenoxy which is substituted by at least one member selected from the group consisting of halogen, cyano, nitro, trifluoromethyl, trifluoromethoxy, trifluoromethylthio, C₁₋₄-alkyl, C₁₋₄-alkylthio, C₁₋₄-alkylthioalkyl, C₁₋₄-alkylsulphonyloxy, phenyl and C₁₋₄-alkoxycarbonyl,
R³ represents hydrogen or chlorine, and
R⁴ represents hydrogen.

3. A compound according to claim 1, wherein such compound is 1-(2-chloro-4-fluoro-benzoyl)-3-(3,5-dichloro-4-(4-cyanophenoxy)-phenyl)-urea of the formula

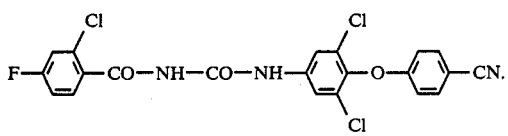

4. A compound according to claim 1, wherein such compound is 1-(2-chloro-4-fluoro-benzoyl)-3-(3,5-dichloro-4-(2-chloro-4-nitrophenoxy)-phenyl)-urea of the formula

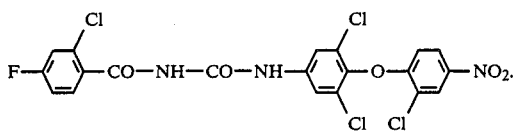

5. A compound according to claim 1, wherein such compound is 1-(2-chloro-4-fluoro-benzoyl)-3-(4-(2-chloro-4-trifluoromethylphenoxy)-phenyl)-urea of the formula

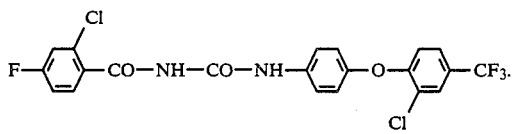

6. A compound according to claim 1, wherein such compound is 1-(2-chloro-4-fluoro-benzoyl)-3-(3-chloro-4-(2-chloro-4-cyanophenoxy)-phenyl)-urea of the formula

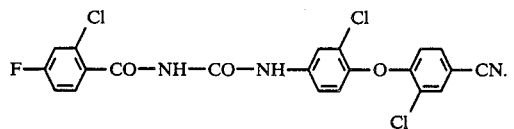

7. A compound according to claim 1, wherein such compound is 1-(2-chloro-4-fluoro-benzoyl)-3-(3-chloro-4-(2,4-dichlorophenoxy)-phenyl)-urea of the formula

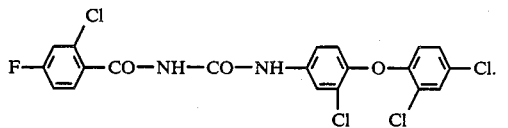

8. A compound according to claim 1, wherein such compound is 1-(2-chloro-4-fluoro-benzoyl)-3-(4-(2-chloro-4-cyanophenoxy)-phenyl)-urea of the formula

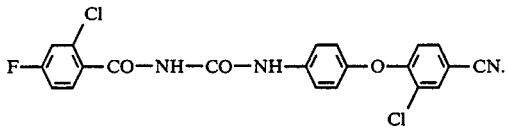

9. A compound according to claim 1, wherein such compound is 1-(2-chloro-4-fluoro-benzoyl)-3-(3,5-dichloro-4-(4-trifluoromethoxyphenoxy)-phenyl)-urea of the formula

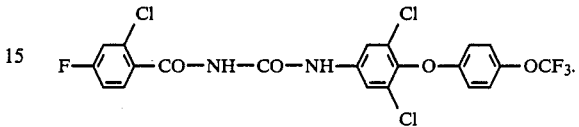

10. A compound according to claim 1, wherein such compound is 1-(2-chloro-4-fluoro-benzoyl)-3-(3,5-dichloro-4-(4-trifluoromethylthiophenoxy)-phenyl)-urea of the formula

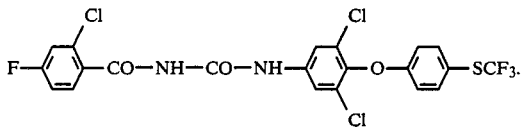

11. A compound according to claim 1, wherein such compound is 1-(2-chloro-4-fluoro-benzoyl)-3-(3,5-dichloro-4-(2-chloro-4-trifluoromethoxyphenoxy)-phenyl)-urea of the formula

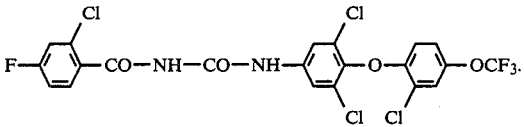

12. An insecticidal composition comprising an insecticidally effective amount of a compound according to claim 1 and a diluent.

13. A method of combating insects which comprises applying to such insects an insecticidally effective amount of a compound according to claim 1.

14. The method according to claim 11, wherein such compound is
1-(2-chloro-4-fluoro-benzoyl)-3-(3,5-dichloro-4-(4-cyanophenoxy)-phenyl)-urea,
1-(2-chloro-4-fluoro-benzoyl)-3-(3,5-dichloro-4-(2-chloro-4-nitrophenoxy)-phenyl)-urea,
1-(2-chloro-4-fluoro-benzoyl)-3-(4-(2-chloro-4-trifluoromethylphenoxy)-phenyl)-urea,
1-(2-chloro-4-fluoro-benzoyl)-3-(3-chloro-4-(2-chloro-4-cyanophenoxy)-phenyl)-urea,
1-(2-chloro-4-fluoro-benzoyl)-3-(3-chloro-4-(2,4-dichlorophenoxy)-phenyl)-urea,
1-(2-chloro-4-fluoro-benzoyl)-3-(4-(2-chloro-4-cyanophenoxy)-phenyl)-urea,
1-(2-chloro-4-fluoro-benzoyl)-3-(3,5-dichloro-4-(4-trifluoromethoxyphenoxy)-phenyl)-urea,
1-(2-chloro-4-fluoro-benzoyl)-3-(3,5-dichloro-4-(4-trifluoromethylthiophenoxy)-phenyl)-urea, and
1-(2-chloro-4-fluoro-benzoyl)-3-(3,5-dichloro-4-(2-chloro-4-trifluoromethoxyphenoxy)-phenyl)-urea.

* * * * *